Figure 1:
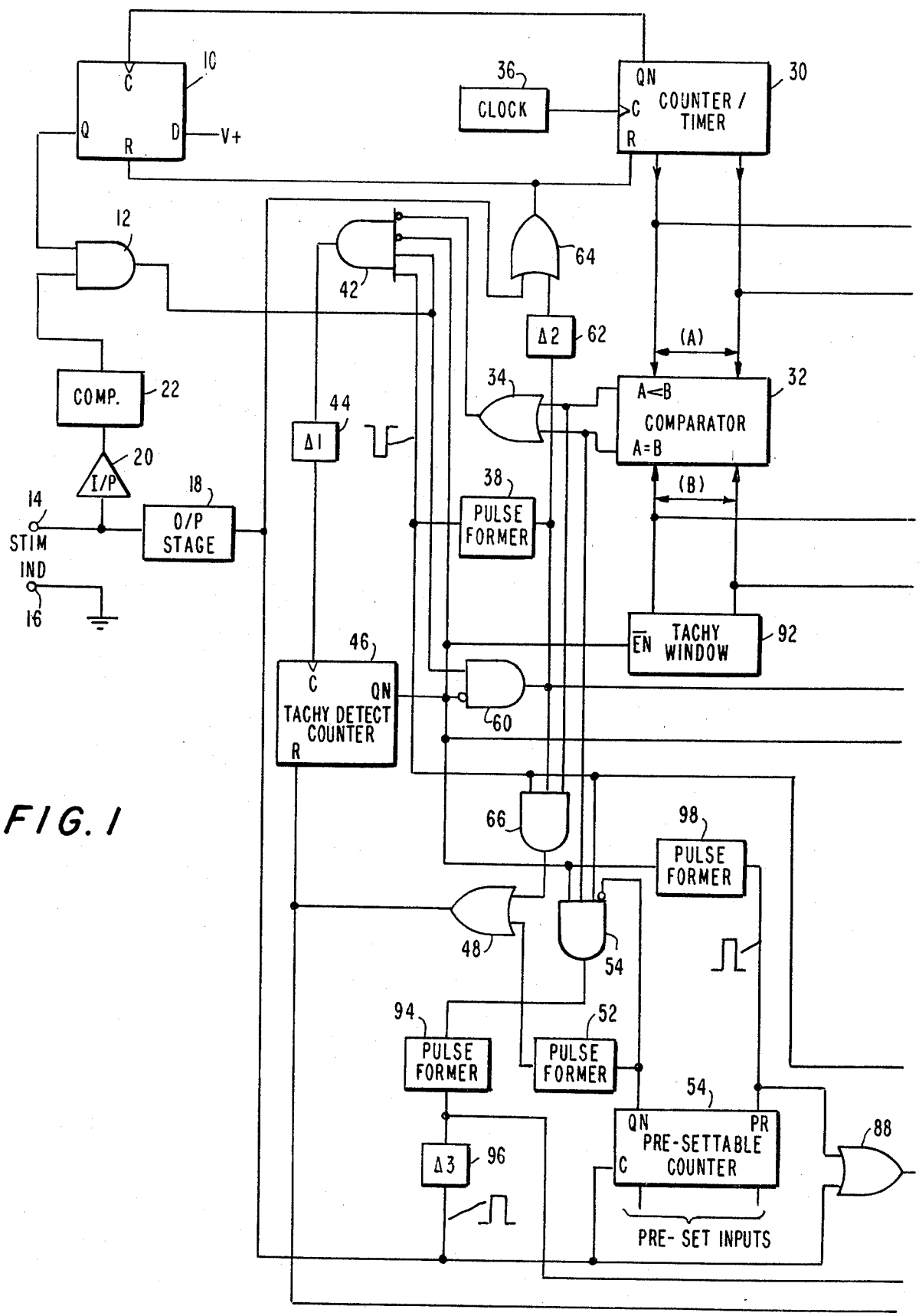

United States Patent [19]
Spurrell et al.

[11] 4,408,606
[45] Oct. 11, 1983

[54] RATE RELATED TACHYCARDIA CONTROL PACER

[75] Inventors: Roworth A. J. Spurrell; Alan J. Camm; David E. Ward, all of London, England

[73] Assignee: Telectronics Pty. Ltd., Lane Cove, Australia

[21] Appl. No.: 245,216

[22] Filed: Mar. 19, 1981

[30] Foreign Application Priority Data

May 19, 1980 [GB] United Kingdom ................. 8016455

[51] Int. Cl.³ .............................................. A61N 1/36
[52] U.S. Cl. ............................................... 128/419 PG
[58] Field of Search ................................. 128/419 PG

[56] References Cited

U.S. PATENT DOCUMENTS 3,638,224  2/1972  Berkovits ..................... 128/419 PG
3,698,398  10/1972  Berkovits ..................... 128/419 PG
3,939,844  2/1976  Pequignot ..................... 128/419 PG
4,163,451  8/1979  Lesnick et al. ............... 128/419 PG Primary Examiner—William E. Kamm
Attorney, Agent, or Firm—Gottlieb, Rackman & Reisman

[57] ABSTRACT

An improved pacer for controlling tachycardia. Following tachycardia confirmation, a burst of at least three stimulating pulses is generated. The time intervals between successive pulses decrease by a fixed decrement; thus the rate of the pulses increases during each cycle of operation, the burst being more accurately characterized as a "chirp". The first pulse is generated following the last heartbeat which is used to confirm tachycardia at a time which is actually dependent on the rate of the heartbeats in the tachycardia episode; the time delay between the last heartbeat and the first pulse in the chirp is equal to the time interval between the last two heartbeats, less the fixed decrement which characterizes successive time intervals between stimulating pulses. Because successive pulses are generated at an increasing rate, and because the first pulse is generated at a time which is actually dependent upon the tachycardia rate, there is a greater likelihood that tachycardia termination will be achieved.

3 Claims, 2 Drawing Figures

RATE RELATED TACHYCARDIA CONTROL PACER

This invention relates to tachycardia control pacers, and more particularly to such pacers which generate stimulating pulse bursts.

Tachycardia is a condition in which the heart beats very rapidly, typically, above 150 beats per minute. There are several different pacing modalities which have been suggested for termination of tachycardia. The underlying principle in all of them is that if a pacer stimulates the heart at least once shortly after a heartbeat, before the next naturally occurring heartbeat at the rapid rate, the heart may successively revert to sinus rhythm. Tachycardia is often the result of electrical feedback within the heart; a natural beat results in the feedback of an electrical stimulus which prematurely triggers another beat. By interposing a stimulated heartbeat, the stability of the feedback loop is disrupted. As with conventional heart pacers, the electrodes of a tachycardia control pacer may be atrially-coupled or ventricularly-coupled. Although the detection of atrial beats and atrial stimulation are preferred, ventricular beat detection and pacing may also be employed.

In the copending application of Spurrell et al, entitled "Two-Pulse tachycardia Control Pacer", Ser. No. 245,215, filed on Mar. 19, 1981, which application is hereby incorporated by reference, there is disclosed a tachycardia control pacer which generates a single stimulus, or two stimuli, following each confirmation of tachycardia. The delay between the last heartbeat which is used to confirm a tachycardia episode and the first stimulus is referred to as the "initial delay", and the interval between the first stimulus and the second (if a second stimulus is generated) is referred to as the "coupled interval". In the Spurrell et al pacer, the physician may program maximum values for the initial delay and the coupled interval. The pacer automatically scans both the initial delay and the coupled interval during successive cycles, both scanning sequences involving fifteen 6-millisecond decrements. The net result is that up to 256 different timed pairs of stimuli may be generated in an effort to terminate tachycardia.

The difficulty in tachycardia control is that there is usually no way of knowing exactly when a stimulating pulse should be applied. One or more pulses should be applied shortly after a heartbeat and prior to the time when the next premature beat would otherwise occur, but there is usually no way of knowing precisely when the pulses should be generated. As an alternative to the Spurrell et al type of control, it has been proposed to generate a single pulse after the last heartbeat in the tachycardia confirmation cycle which is related to the heartbeat rate. By keying the single pulse which is generated to the actual rate at which the heart is beating, the single pulse which is generated is more likely to terminate tachycardia. Nevertheless, it has been found that such a single-pulse technique is not maximally effective.

It is an object of our invention to provide a more effective pulse stimulation sequence for terminating tachycardia, a sequence which is related to the rate of the heartbeats in the tachycardia episode.

In accordance with the principles of our invention, a burst of at least three pulses is generated following each tachycardia confirmation. The time intervals between pulses keep decreasing; the pulse rate thus continuously increases and the overall sequence is more accurately characterized as a "chirp" since its rate continuously increases. The successive time intervals between pulses decrease by the same fixed decrement. This type of increasing pulse rate during a single cycle of operation has been found to be effective in controlling tachycardia; the acceleration of pacing over a short interval results in stimulation at different phases of a tachycardia cycle and thus a greater likelihood of generating a pulse at the right time. Most important is the fact that the initial time interval, between the last heartbeat used to confirm tachycardia and the first pulse in the sequence, is related to the rate of the heartbeats and is equal to the heartbeat rate less the fixed decrement.

Thus suppose, for example, that during a particular tachycardia episode the heart is beating at 300-millisecond intervals. If the fixed decrement selected is 10 milliseconds, the first pulse which will be generated will occur 290 milliseconds after the last heartbeat in the tachycardia confirmation cycle. The next pulse to be generated will occur 280 milliseconds later, etc. A predetermined number of pulses is generated. However, should the number of pulses which is generated, the fixed decrement and the initial heartbeat rate be such that the time intervals between successive pulses toward the end of the sequence would otherwise fall below a minimum "safe" value (which might result in fibrillation), the last pulses in the sequence are generated at a fixed rate above the minimum safe value. Thus in the illustrative embodiment of the invention the same number of pulses is always generated during each cycle of operation, although the pulses at the end of the cycle may be generated at a fixed maximum rate should the successive decrementing of the time intervals between pulses result in the pulses being generated at too fast a rate. (A typical minimum inter-pulse interval is 200 milliseconds, a fixed decrement of 5 or 10 milliseconds is preferred, and we contemplate the generation of a predetermined number of pulses in the 10–20 range. Alternatively, instead of generating a fixed number of pulses, the pulses might be made to cease after they are generated for a predetermined length of time.)

Figure 2:
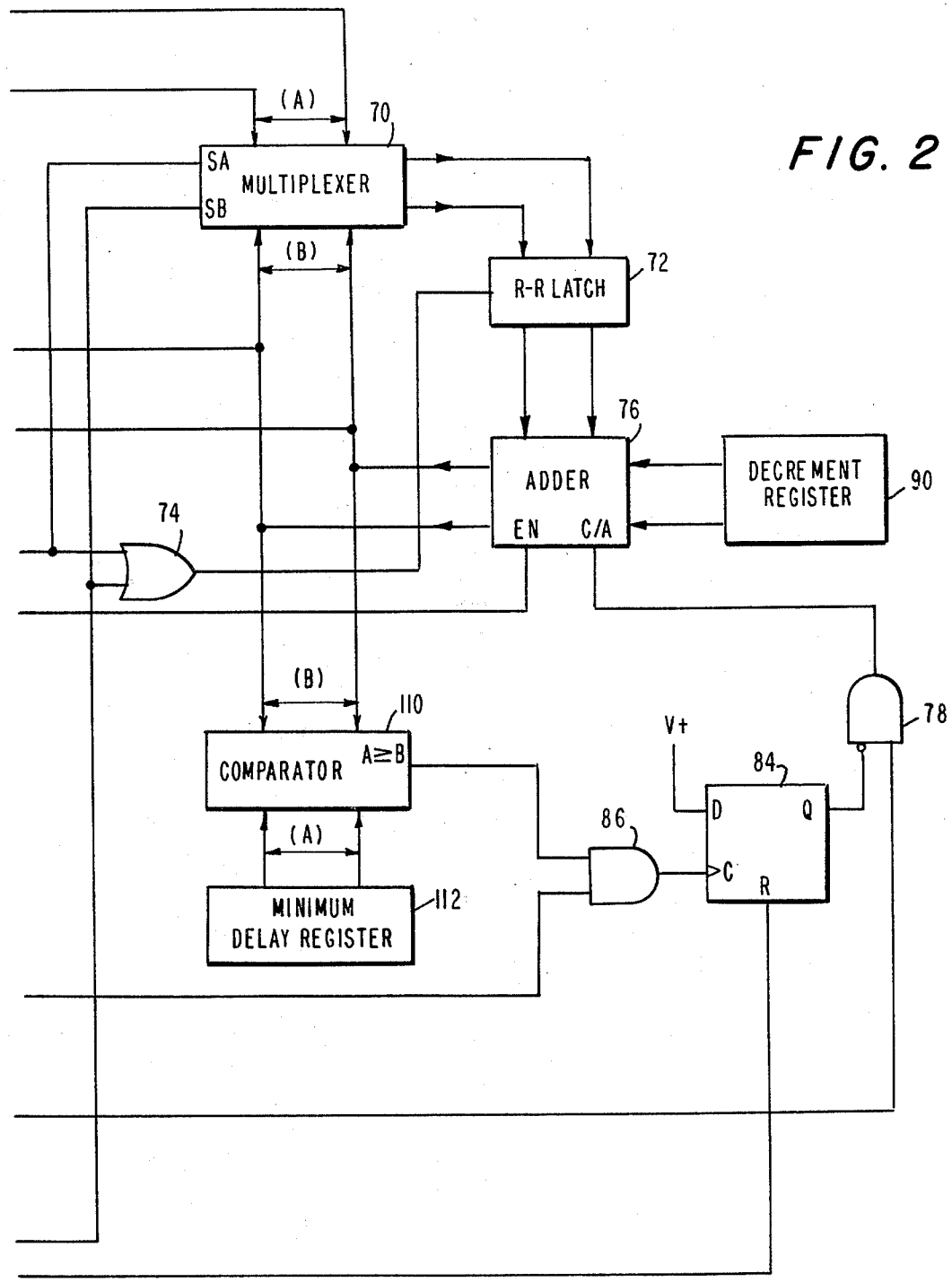

Further objects, features and advantages of our invention will become apparent upon consideration of the following detailed description in conjunction with the drawing, in which:

FIGS. 1 and 2, with FIG. 1 being placed to the left of FIG. 2, depict the illustrative embodiment of the invention.

The pacer includes a pair of electrodes, the indifferent electrode being shown by the numeral 16 on FIG. 1 and the stimulating electrode being shown by the numeral 14. Output stage 18 is a conventional heart pulser which applies a pulse to the stimulating electrode each time that a trigger pulse appears at its input. Input stage 20 and comparator 22 are also conventional heart pacer circuits and they serve to detect heartbeats, each heartbeat resulting in the output of comparator 22 being pulsed high.

The basic timing component is counter/timer 30, which is driven by clock 36. As will be described below, each heartbeat which is detected results in the resetting of the counter/timer. Within a 100-millisecond refractory period following each heartbeat, any signal detected by input stage 20 is ignored; this is a standard heart pacer technique which prevents multiple "detections" of the same heartbeat. Flip-flop 10 disables gate 12 for 100 milliseconds after each heartbeat is detected.

The same pulse at the output of gate 64 which resets counter/timer 30, as will be described below, also resets flip-flop 10. Thus each heartbeat which is detected results in resetting of the flip-flop, with the Q output going low to disable gate 12. With the counter/timer now reset, it starts to count upward. After 100 milliseconds have elapsed, the QN output of the counter/timer goes high. Flip-flop 10 is thus clocked and, since a high potential is applied to its D input, the Q output goes high to enable gate 12 once again.

When the output of gate 60 first goes high upon the detection of each heartbeat, as will be described below, the output of pulse former 38 goes low momentarily after a short delay. But when the output of gate 60 first goes high, the output of pulse former 38 is high to enable one input of gate 42. The QN output of tachy detect counter 46 is normally low in potential, and it is applied to one of the inverting inputs of gate 42 so that a second input of the gate is normally enabled. Pulses at the output of gate 12 are applied to a third (non-inverting) input of gate 42. Thus each heartbeat which is detected results in the output of gate 42 going high, provided that the inverting input of gate 42 which is connected to the output of gate 34 is low at that time.

When the heart is beating in sinus rhythm, however, the output of gate 34 is high, and heartbeats do not result in the output of gate 42 being pulsed high. There are two inputs to comparator 32. The B inputs are derived from tachy window register 92. This register, with tri-state outputs, is normally enabled by the low potential at the QN output of tachy detect counter 46. (The tri-state outputs of adder 76 have no effect on the B inputs of comparator 32 at this time, since the adder outputs are disabled by the low potential at the QN output of counter 46.) Register 92 contains a count which represents the minimum time spacing between normal heartbeats, typically, 375 milliseconds. It is only if heartbeats occur more rapidly that they are considered to be part of a tachycardia eposide (provided that a minimum number of such pulses are detected in succession). The tachy window outputs are applied to the B inputs of comparator 32. The other inputs, the A inputs, are controlled by the outputs of counter/timer 30. Provided that the heart is beating in sinus rhythm, counter/timer 30 will have counted to a value greater than that represented by register 92 when a heartbeat is detected. Thus although gate 12 operates to indicate detection of a heartbeat, one of the A=B or A>B (usually, the latter) outputs of comparator 32 will be high, and the output of gate 34 will be high to disable gate 42. Consequently, as long as the heart is beating normally, gate 42 does not pulse its output. Each heartbeat simply results in the resetting of the counter/timer and flip-flop 10. Since the QN output of counter 46 is low to enable gate 60, each pulse at the output of gate 12 is extended through gate 60, delay element 62 and OR gate 64 to reset the flip-flop and the counter/timer.

But should the heart be beating at a rate rapid enough to be considered as part of a tachycardia episode, depending upon the value stored in register 92, then when gate 12 operates the counter/timer will not have counted up to the value represented in register 92. Consequently, the B inputs to the comparator will be greater than the A inputs, and both comparator outputs will be low. With the output of gate 34 low, the respective input of gate 42 is enabled, and the gate output is pulsed high when a heartbeat is detected. After a short delay introduced by delay element 44, the count in tachy detect counter 46 is incremented. This is the counter which is used to detect a predetermined number of successive heartbeats, all of which occur at a rate greater than that represented by tachy window register 92. Typically, at least five such successive rapid heartbeats must be detected before tachycardia is confirmed, at which time the QN output of counter 46 goes high to control a pulse generation cycle.

The reason for providing delay element 44 is that when the QN output of counter 46 goes high, gate 60 is disabled and its output goes low. Thus the pulse at the output of gate 60 which is derived from the pulse at the output of gate 12 would terminate as soon as the QN output of counter 46 goes high. In order that the pulse not terminate prematurely since it must perform other functions, delay element 44 is provided to prevent gate 60 from being disabled until the pulse at the output of gate 12 has terminated.

It should be observed that whenever the output of gate 60 goes high upon the detection of a heartbeat, the output of pulse former 38 goes low momentarily. While normal heartbeats are being detected, the A inputs to comparator 32 are greater than the B inputs when the output of gate 12 goes high; since the output of gate 34 is thus high, gate 42 does not operate. But the positive pulse at the output of gate 60 results in the resetting of counter/timer 30 and at this time the A=B and A>B outputs of the comparator both drop low. The resetting of the counter/timer might thus result in the pulse at the output of gate 12 being transmitted through gate 42 even for a heartbeat in sinus rhythm. To prevent this, pulse former 38 generates a short negative pulse after the output of gate 60 first goes high. By the time the outputs of counter/timer 30 represent a value of 0 as a result of the resetting by gate 64, the output of pulse former 38 is low so that gate 42 cannot operate. By the time the output of pulse former 38 reverts high once again, the output of gate 12 is low. In order that gate 42 operate when rapid beats are detected, the output of pulse former 38 does not go low immediately when the output of gate 60 goes high. It is delayed slightly so that the pulse at the output of gate 12 can be transmitted through gate 42 should the output of gate 34 be low when a heartbeat is detected. Thus the output of pulse former 38 goes low only after the pulse at the output of gate 12 has controlled the outputs of gates 60 and 42; the pulse former output then prevents erroneous operations which might otherwise occur from the resetting of counter/timer 30.

It is necessary to store the count in counter/timer 30 which represents the last inter-beat interval because this count represents the rate at which heartbeats are occurring, and the heartbeat rate is used to control the initial rate at which stimulating pulses are generated. Each positive pulse which appears at the output of gate 60 is extended through gate 74 to the enable input of R-R latch 72. This latch is used to store the count in counter/timer 30. (The terminology "R-R latch" is used to refer to the fact that what is stored is a count corresponding to the time interval between successive R waves, although if the stimulating electrode is connected to the patient's atria, then it is really the interval between P waves which is stored.) The same pulse at the output of gate 60 is extended to the SA ("select A") input of multiplexer 70. When this input is pulsed high, the multiplexer extends its set of A inputs to the outputs which are connected to the inputs of the R-R latch. Consequently, the last count in counter/timer 30 is extended through the multiplexer and stored in the R-R latch.

Every pulse at the output of gate 12 following the detection of a heartbeat is extended through gate 60, prior to tachycardia confirmation, and thus the output of gate 60 goes high. After a delay introduced by delay element 62, the pulse is extended through OR gate 64 to reset both counter/timer 30 and flip-flop 10. This resetting takes place as long as normal heartbeats are being detected, and while counter 46 is counting the number of rapid beats which comprise a tachycardia confirmation cycle. The last heartbeat in the tachycardia confirmation cycle results in the disabling of gate 60 when the QN output of counter 46 goes high. But this last heartbeat does result in the output of gate 60 going high and the resetting of counter/timer 30 in the usual way. The count in counter/timer 30 must be extended through multiplexer 70 and latched in latch 72 before the counter/timer is reset. That is the reason for providing delay element 62; the counter/timer is not reset until after a sufficient time has elapsed to allow the count to be stored in latch 72.

It should be noted that every time gate 12 operates, as long as gate 60 is held enabled by counter 46, the count in counter/timer 30 is stored in latch 72, since the output of gate 60 goes high during normal heartbeat detection and during the detection of heartbeats which comprise a tachycardia episode, until the predetermined number of such heartbeats have been detected and gate 60 is disabled. However, the successive storage of counts in latch 72 does not affect the system operation. What is important is the delivery of the latch contents to adder 76, and this is controlled by the operation of gate 78. Whenever the output of the gate goes high and pulses the clear and add (C/A) input of adder 76, the count in latch 72 is delivered to adder 76, and the contents of decrement register 90 are added to it in the adder. The decrement register contains a twos complement representation of the fixed decrement which characterizes successive time intervals which separate stimulating pulses. Thus the adder really functions as a subtractor, and the first time that gate 78 operates, the value represented at the outputs of the adder is equal to the last count of counter/timer 30, minus the fixed decrement. The Q output of flip-flop 84 is normally low in potential, as will be described below, to enable one input of gate 78. When the QN output of counter 46 goes high to indicate tachycardia confirmation, pulse former 98 generates a short positive pulse, as indicated in the drawing. This pulse is extended through OR gate 88 to the other input of gate 78, to control the first operation of adder 76.

Thus far it has been assumed that tachy detect counter 46 counts five rapid beats in succession, each beat resulting in a count in counter/timer 30 which is less than that represented by register 92. But should any heartbeat occur after the preceding heartbeat with an inter-beat interval which exceeds that which is represented by register 92, the tachycardia confirmation cycle is aborted and tachy detect counter 46 is reset. In such a case, the A>B output of comparator 32 is high when the beat is detected, and thus enables one input of gate 66. Another input of gate 66 is connected to the output of gate 60 which goes high when the beat is detected (until such time that tachycardia is confirmed and the gate is disabled by the QN output of counter 46), and the third input of gate 66 is connected to the output of pulse former 38 which remains high when the output of gate 60 first goes high. Consequently, the output of gate 66 is pulsed high, and the pulse is transmitted through gate 48 to reset counter 46. The pulse at the output of gate 48 also resets flip-flop 84. It is for this reason that the Q output of the flip-flop is low as originally assumed above. Every normal beat, even such a beat which occurs while a number of premature beats have been counted (but less than the number which represents tachycardia confirmation), results in the resetting of counter 46 and flip-flop 84.

As soon as tachycardia is confirmed, the output of gate 60 remains low. Consequently, the SA input of multiplexer 70 remains low, and the count in counter/timer 30 is no longer extended to latch 72 through the multiplexer. Similarly, counter/timer 30 can no longer be reset by pulses at the output of gate 60, which pulses represent heartbeats. These pulses are extended through delay element 62 and OR gate 64 only before counter 46 has confirmed tachycardia. Once tachycardia has been confirmed, the QN output of the counter goes high to disable gate 60. Nor can gate 66 control the resetting of the counter since the output of gate 60 is low and disables it. As will be described below, counter 46 is reset only after the predetermined number of pulses have been delivered.

This number is pre-set by the physician. Pre-settable counter 54 is provided with pre-set inputs which control the storage in the counter of a value whenever the pre-set (PR) input is pulsed. Pulse former 98 pulses the PR input when the QN output of counter 46 first goes high hollowing tachycardia confirmation. The value which is pre-set in the counter is not the number of pulses which is to be generated in each chirp, but rather the complement of this number relative to 20. Counter 54 increments its count whenever its clock (C) input is pulsed high. When a maximum count of 20 is reached, the QN output of the counter goes high and terminates the pulse sequence. Thus, for example, if 15 pulses are to be generated in each chirp, the pre-set inputs would be tied to potentials which control the pre-setting in the counter of a count of 5. It will thus take 15 stimulating pulses before the QN output of the counter goes high to terminate the pulsing sequence.

Comparator 32 no longer functions to compare the count in counter/timer 30 with the values stored in register 92. That is because the register is now disabled since its EN input is high as a result of the QN output of counter 46 being high. The outputs of register 92 are tri-stated so that they have no effect on the overall system operation. Comparator 32 now functions to compare the count in counter/timer 30, at the A inputs, with the value stored in adder 76, applied to the B inputs of the comparator. It will be recalled that the initial value contained in adder 76 is the last R-R interval, less the fixed decrement represented by register 90.

The last heartbeat, the one which results in tachycardia confirmation, resets counter/timer 30 in the usual way. The counter then starts counting once again under control of clock 36. When the count equals the value represented at the outputs of adder 76, the A=B output of comparator 32 goes high. This causes one input of gate 54 to go high. The inverting input of the gate is normally enabled by the QN output of counter 54, which is low until the pre-set number of pulses has been generated. A third input of gate 54 is connected to the output of pulse former 38 which remains high in potential since its output is pulsed low only responsive to the output of gate 60 going high, and the output of gate 60 is held low during the pulse generation sequence. The fourth input of gate 54 is connected to the QN output of counter 46 which is high in potential during the pulse generation sequence. Consequently, the output of gate 54 goes high whenever comparator 32 determines that the count in counter/timer 30 equals the value represented in adder 76.

When the output of gate 54 goes high, pulse former 94 generates a positive pulse at its output. This pulse is applied to the SB ("Select B") input of multiplexer 70 which thus extends its B inputs to the outputs connected to R-R latch 72. The same pulse is extended through gate 74 to the enable input of the latch. Consequently, the value stored in adder 76 is transferred to the latch. Shortly thereafter, delay element 96 generates a positive pulse at its output. (The delay is provided to allow the latching operation to be completed first.) This pulse controls four functions.

First, the pulse is applied to the input of output stage 18, so that a stimulating pulse is generated. Second, the pulse is applied to an input of gate 64 to reset counter/timer 30 so that another timing cycle can begin. Third, the pulse is applied to the clock input of counter 54 to increment its count. Fourth, the pulse is extended through OR gate 88 and gate 78 to the clear and add input of adder 76. The previous contents of the adder, which are now contained in latch 72, are re-stored in the adder and reduced by the value of the fixed decrement contained in register 90. Adder 76 now represents the next required inter-pulse time interval. The timing cycle begins all over again, and when the A=B output of comparator 32 goes high, another stimulating pulse is generated.

When the last pulse in the sequence has been generated, the QN output of counter 54 goes high. The high output disables gate 54 so that no more stimulating pulses are generated. Pulse former 52 now generates a short pulse which is extended through OR gate 48 to the reset input of counter 46. The QN output of the counter goes low once again to enable gate 60. The system assumes that tachycardia has been terminated. If this is not the case, counter 46 will count five rapid beats, and another overall pulse generation cycle will ensue. Until such time that tachycardia is confirmed again, the QN output of counter 54 remains high to disable gate 54. It is only when the QN output of counter 46 goes high to indicate tachycardia confirmation that pulse former 98 controls the pre-setting of counter 54 and the enabling of gate 54 once again.

Flip-flop 84 is normally reset. Every operation of gate 48 results in the resetting of the flip-flop. When the flip-flop is reset, its Q output is low so that gate 78 operates as described above. It is only when gate 86 operates to clock the flip-flop that the Q output goes high to disable gate 78, since the D input of the flip-flop is connected to a positive potential.

Minimum delay register 112 contains a count which represents the maximum safe pulsing rate. In the case of ventricular stimulation, register 112 contains a count which corresponds to a minimum inter-pulse interval of 220 milliseconds, and in the case of atrial stimulation it contains a count which represents a minimum inter-pulse interval of 180 milliseconds. The contents of adder 76 represent the inter-pulse interval to be controlled at any instant of time during a pulse sequence. As long as the inter-pulse interval to be controlled is greater than the minimum safe value, the A inputs of comparator 110 represent a value which is less than the value represented at the B inputs, and the $A \geq B$ output of the comparator is low. Consequently, the output of gate 86 remains low and flip-flop 84 remains reset. However, if the time interval represented in adder 76 is less than the minimum value, the $A \geq B$ output goes high to enable one input of gate 86. The other input of the gate is connected to the output of pulse former 38 which is normally high in potential. (Pulse former 38 is provided simply to prevent erroneous operations of several gates as a result of comparators 32 and 110 otherwise operating in an indeterminate fashion when counter/timer 30 is reset or adder 76 has its count changed.) As soon as the output of gate 86 goes high to clock flip-flop 84, the Q output goes low. The system continues to operate as described above, but the C/A input of adder 76 is no longer pulsed whenever a stimulating pulse is generated. Consequently, adder 76 retains in it the last inter-pulse time value prior to the output of comparator 110 going high. The last pulses in the preset number of pulses determined by counter 54 are generated at the same rate, that is, with the last inter-pulse interval which resulted from the last decrementing of the count in adder 76 (an interval which is above the minimum safe value).

It should be noted that when register 92 is enabled rather than adder 76, prior to tachycardia confirmation, the outputs of register 92 are applied to the B inputs of comparator 110. This is of no moment, however, because register 92 represents an inter-beat interval which is used to detect tachycardia and, that interval, while it may be adjusted by the physician, is always greater than the minimum safe inter-pulse interval represented by register 112. Consequently, the $A \geq B$ output of comparator 110 is low and flip-flop 84 remains reset.

There are several different parameter values which control the pacer operation. Although these can be fixed during manufacture of the device, it may be preferred to allow the physician to program the values under external control. The paramater values of this type include those contained in tachy window register 92, pre-settable counter 54, minimum delay register 112 and decrement register 90. Conceivably, the physician might even want to program the number of successive rapid beats which must be counted by counter 46 to constitute tachycardia confirmation. Although the illustrative pacer disclosed in the drawing does not allow such programming, techniques for accomplishing parameter value changes under external control are well known to those skilled in the art. Reference may be had to the above-identified Spurrell et al application for a thorough description of the manner in which parameter values may be adjusted under external control.

Furthermore, although the pacer has been described as working with fixed time-interval decrements (even if the decrement can be programmed by the physician, once the programming is accomplished the decrement value remains fixed), it is possible to provide for scanning of decrement values during successive cycles using a scanning technique such as that disclosed in the above-identified Spurrell et al application. In such a case, following tachycardia confirmation, a pulse chirp would be generated while employing some value of time-interval decrement. If tachycardia is terminated, this same (successful) decrement can be used following the next tachycardia confirmation. But if tachycardia has not been terminated, then the decrement might be changed at the start of the next cycle. The decrement could thus be scanned over some desired range, with the decrement value changing by perhaps several milliseconds from cycle to cycle. Successful termination of tachycardia could be detected using the same technique as disclosed in the above-identified Spurrell et al application; following a pulse generation cycle, if any heartbeat is detected which follows the preceding beat by a time interval greater than that represented in register 92, then the decrement would not be changed following the next tachycardia confirmation. Only if a normal heatbeat is not detected between the end of a pulse cycle and the next tachycardia confirmation would the decrement be changed so that a new value might be tried.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

What we claim is:

1. A tachycardia control pacer comprising means for confirming tachycardia, means responsive to each operation of said confirming means for generating a sequence of at least three heart stimulating pulses, means for controlling successive heart stimulating pulses in said sequence to be generated after decreasing time intervals, means for registering the last interval between heartbeats prior to the operation of said confirming means, means for controlling the first pulse in said sequence to be generated at the end of a first time interval following the last heartbeat which is equal to said registered interval less a predetermined value, the successive pulses in said sequence being generated after decreasing time intervals starting with said first time interval, means for controlling the same number of pulses to be generated during each pulse sequence, and means for preventing the pulses toward the end of any sequence from being generated after time intervals which are less than a predetermined interval.

2. A tachycardia control pacer in accordance with claim 1 wherein successive time intervals between the pulses in said sequence differ by said predetermined value.

3. A tachycardia control pacer in accordance with claim 1 wherein said confirming means operates to confirm tachycardia responsive to a predetermined number of heartbeats occurring in succession, each of which occurs after the preceding heartbeat within a predetermined time period.

* * * * *